US00PP09179P

United States Patent [19]

Kotobuki et al.

[11] Patent Number: Plant 9,179

[45] Date of Patent: Jun. 27, 1995

[54] JAPANESE PEAR TREE 'HOUGETSU'

[75] Inventors: Kazuo Kotobuki; Yoshihiko Sato; Kazuyuki Abe; Toshihiro Saito, all of Tsukuba; Isao Shimura, Machida; Kanetsugu Seiko, Kawasaki; Mitsuo Omura, Shizuoka; Ichiro Kajiura, Shimizu; Yutaka Machida; Akio Kurihara, both of Tsuchiura; Tatsushi Ogata, Nagasaki; Teruo Kozono, Miyazaki, all of Japan

[73] Assignees: Fruit Tree Research Station; Ministry of Agriculture, Forestry and Fisheries, Tsukuba, Japan

[21] Appl. No.: 213,595

[22] Filed: Mar. 16, 1994

[51] Int. Cl.[6] ..... A01H 5/00

[52] U.S. Cl. ..... Plt./36

[58] Field of Search ..... Plt. 36

[56] References Cited

PUBLICATIONS

J. Japan. Soc. Hort. Sci. Suppl. 1; Apr., 1993, pp. 142 to 143.

*Primary Examiner*—James R. Feyrer

*Attorney, Agent, or Firm*—Armstrong, Westerman, Hattori, McLeland & Naughton

[57] ABSTRACT

Disclosed is a Japanese pear tree bearing fruit with yellow-reddish-brown skin; having good vigor, a stout shoot, high resistance to black spot disease, and high productivity. This tree produces circular-shaped fruit which mature late in the season (i.e., from the middle to end of October), in the central part of the Kantō district of Japan. This fruit is large, with an average weight of 607 g. The white flesh is soft, crisp, and very juicy. This flesh has a moderate Brix (the pH of the juice being about 4.32) and no aromatic flavor: thus, it possesses excellent dessert quality.

4 Drawing Sheets

BACKGROUND OF THE VARIETY

The present invention relates to a new and distinct variety of Japanese pear tree (*Pyrus pyrifolia*) bearing fruit with a yellow-reddish-brown skin, having a round fruit shape, having moderate acidity, having a moderate keeping quality, and having strong resistance to black spot disease, as well as having high productivity.

In Japan, excellent Japanese pear tree cultivars, including "Kōsui", "Shinsui", and "Hosui" known as "Sansui", have been bred. The trees bear a fruit with a yellowish-brown skin, and producers of pears were able to cultivate both early and mid-season varieties of said pear trees. In particular, an excellent early cultivar known as "Shinsui" has been bred. However, the variety has a productivity problem. Thus, "Chikusui" a new variety, has been bred of to replace "Shinsui". Regarding a late cultivar: though "Shinko", "Okusankichi", etc. have been bred, these latter cultivars have a lower productivity than that of the main cultivars including "Kōsui" and Hōsui", which bear fruit with yellowish-brown skin. Thus, a new late cultivar, having excellent quality and high productivity, is required, instead of said "Shinko" and "Okusankichi" varieties.

One purpose of our breeding program is to provide improved varieties of pear fruit trees, which can be picked late in the season have high productivity; and have high resistance to black spot disease.

ORIGIN AND ASEXUAL REPRODUCTION OF THE VARIETY

The new variety of Japanese pear tree is a cross-seedling which originated from a crossing between "Okusankichi" (♀) which is a late cultivar bearing a fruit with a yellow-reddish-brown skin and having strong acidity and spindle-shaped fruit and "75-23" (♂) which was derived from crossing "Nijisseiki" and "Ri-14" and is a mid-season variety bearing fruit with a yellowish green skin, in 1974, at the Horticultural Research Station of the Ministry of Agriculture, Forestry, and Fisheries, in Hiratsuka-shi, Kanagawa-ken, Japan. The tree was kept in a nursery for a long time, and then was planted, in 1977, at the Research Station in Tsukuba-shi, Ibaraki-ken, Japan. The tree bore fruit for the first time in 1981; and the quality of the fruit corresponded to the above-mentioned purpose. Accordingly, the tree was selected as the first selection in 1982 and was subjected to local adaptability tests, beginning in 1983. These tests were conducted at 25 of the experimental stations in the main Japanese pear-growing regions such as Saitama-ken, and Tottori-ken, under the strain number "Tsukuba No. 40". As a result, the new variety of Japanese pear tree according to this invention was judged to be an excellent new cultivar and was named "Hougetsu" in 1992, and was registered on Jul. 17, 1992 under registration number 16.

This new and distinct variety of Japanese pear tree "Hougetsu" was asexual reproduced by grafting, at the Fruit Tree Research Station, Ministry of Agriculture, Forestry and Fisheries, at 2-1, Fujimoto, Tsukuba-shi, Ibaraki-ken, Japan. The homogeneity and stability of "Hougetsu" of this invention was confirmed.

An application for this new variety of Japanese pear tree "Hougetsu", under the Seeds and Seedling Law of Japan, was filed on Mar. 30, 1992.

SUMMARY OF THE VARIETY

This new variety of Japanese pear tree has strong vigor; a stout shoot; many spurs; and little development of axillary vegetative buds. These characteristics are the same as those of "Okusankichi"; "Hougetsu" has almost the same late-flowering time as "Okusankichi"; and "Hougetsu" is highly-resistant to black spot disease. The tree produces a round-shaped fruit which matures late in the season (i.e., from the middle to end of October), in the central part of the Kantō district in Japan.

The average maturation period of "Hougetsu" is about two weeks earlier than "Okusankichi". The fruit is large, having almost the same weight as "Okusankichi", (i.e., about 600 g; has yellow-reddish-brown skin; has white flesh which is soft and crisp, and has a good keeping quality. The fruit juice has a moderate Brix; and has a moderate acidity at a pH of about 4.4.

DESCRIPTION OF THE VARIETY

Figure 1:
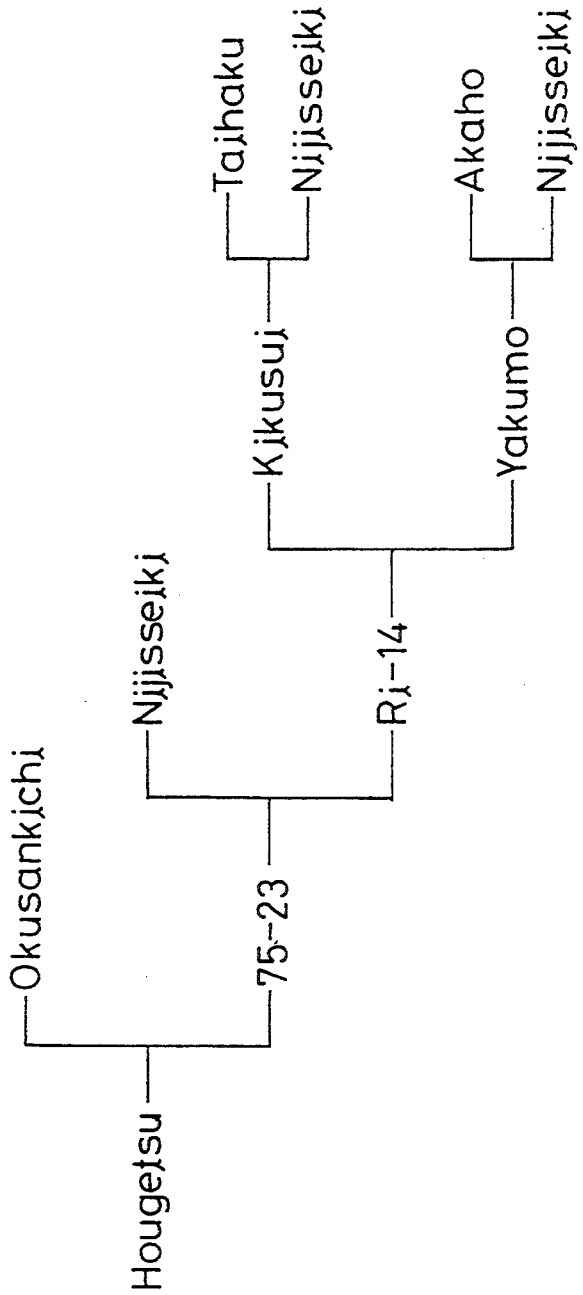
FIG. 1 gives the pedigree of the new and distinct variety of Japanese pear tree "Hougetsu"
Figure 2:
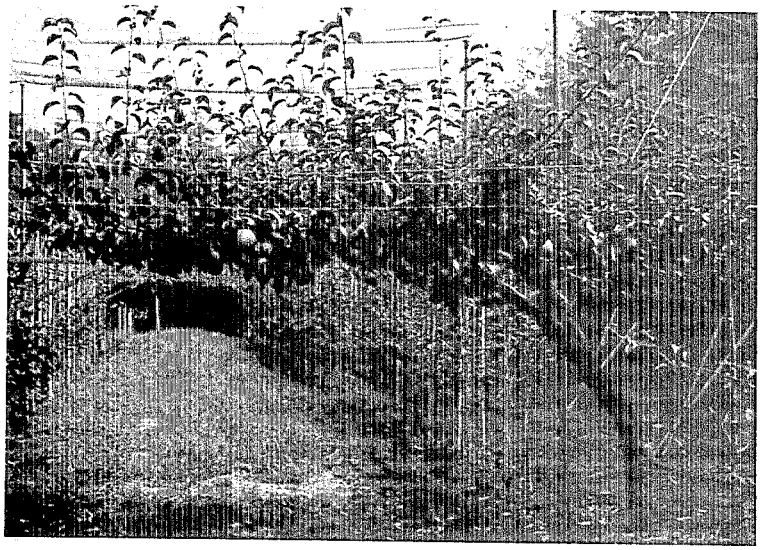
FIG. 2 is a photograph of a shape of the new variety of Japanese pear tree.
Figure 3:
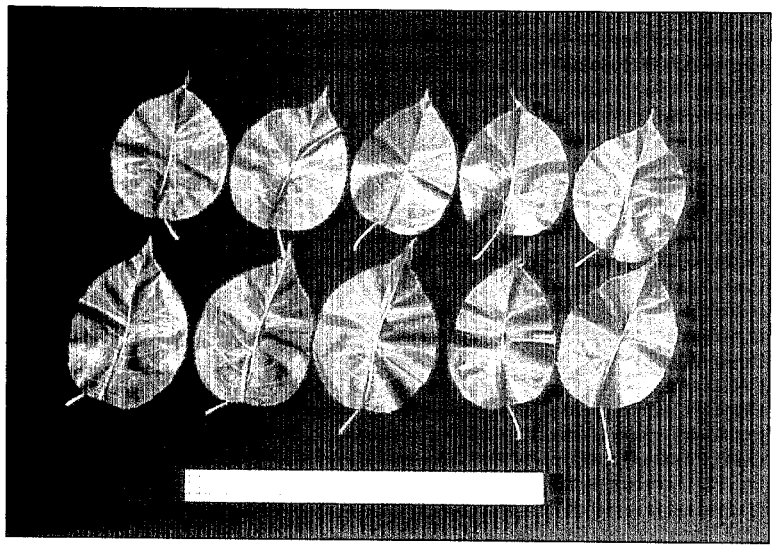
FIG. 3 is a photograph of adult leaves, the upper row being adaxial of the new variety of Japanese pear tree.
Figure 4:
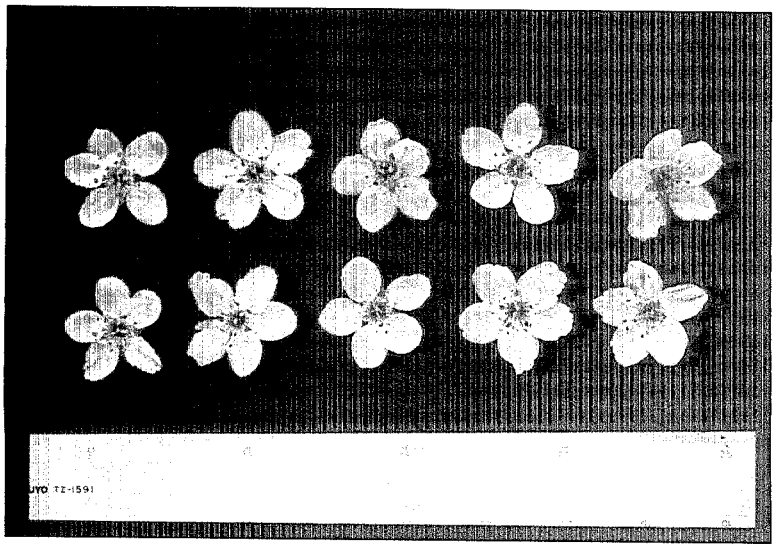
FIG. 4 is a photograph of the flower of the new variety of Japanese pear tree.
Figure 5:
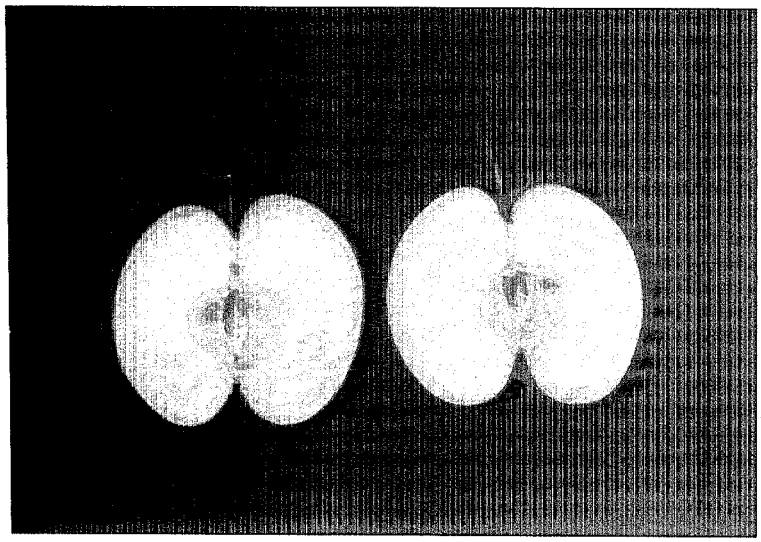
FIG. 5 is a photograph of longitudinal-sectional views of fruit of the new variety of Japanese pear tree.
Figure 6:
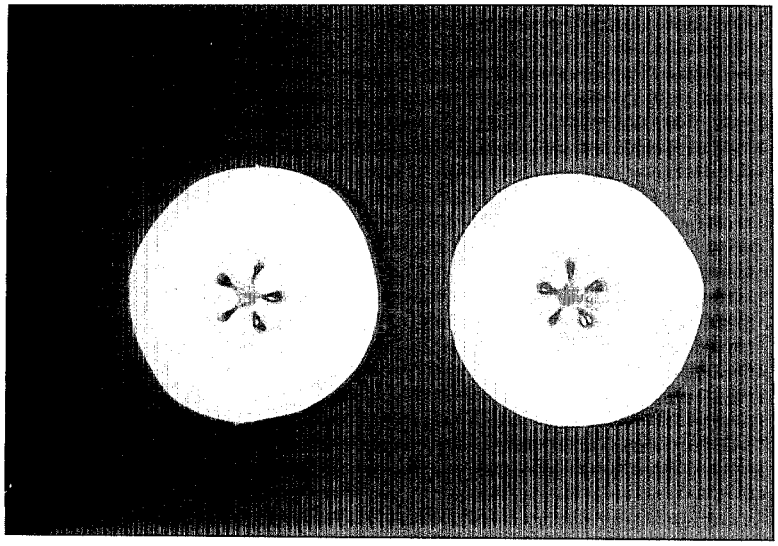
FIG. 6 is a photograph of cross-sectional views of fruit of the new variety of Japanese pear tree.
Figure 7:
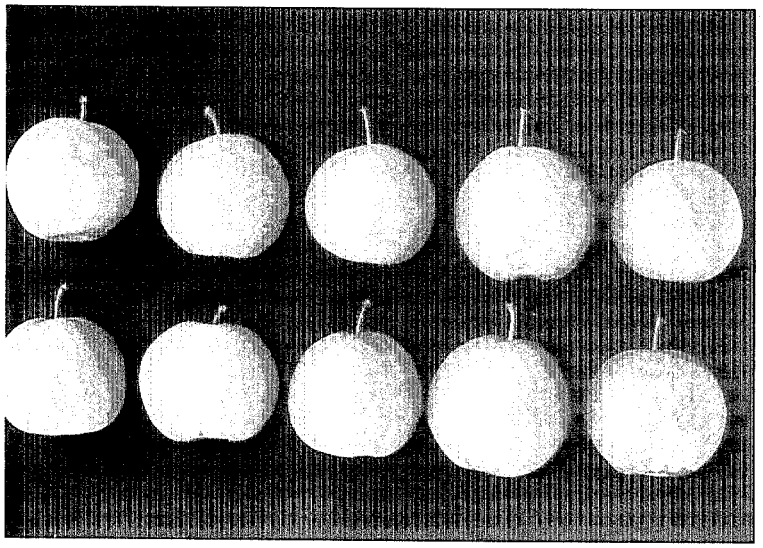
FIG. 7 is a photograph of a side view of the fruit of the new variety of Japanese pear tree.
Figure 8:
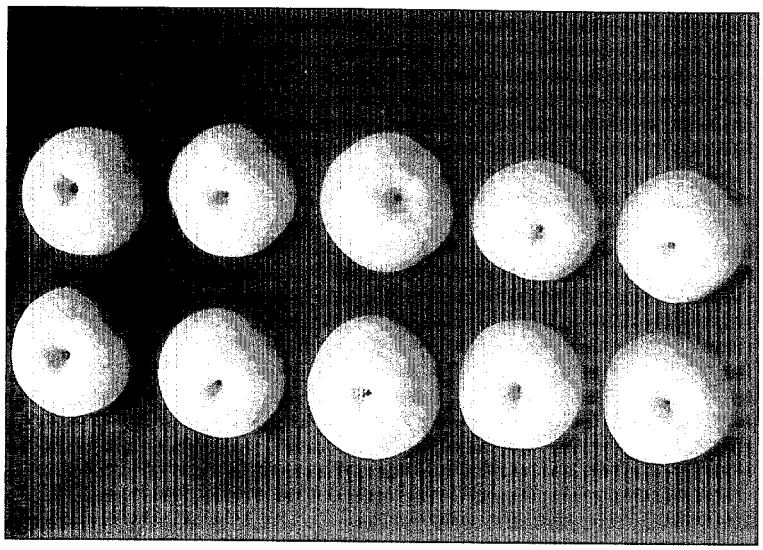
FIG. 8 is a photograph of a styler end of the fruit of the new variety of Japanese pear tree.
Figure 9:
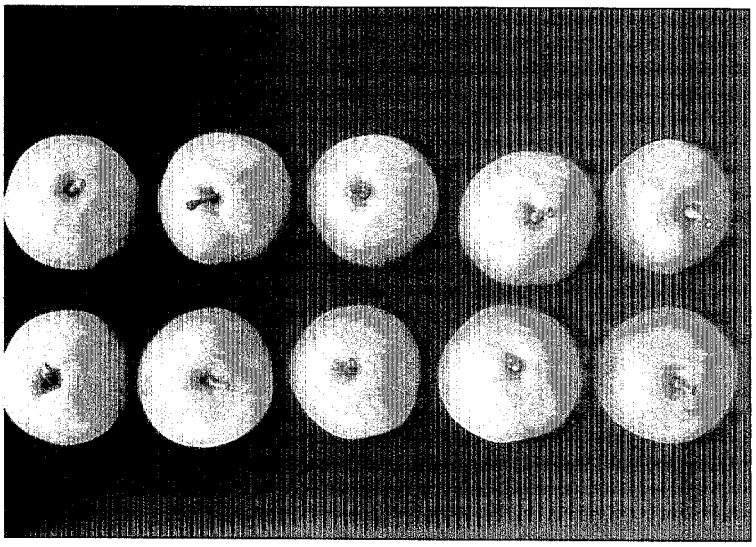
FIG. 9 is a photograph of a basel end of the fruit of the new variety of Japanese pear tree.

The characteristics of the new and distinct variety of Japanese pear tree, "Hougetsu", are as follows (herein, ISCC-NBC is an abbreviation for "Inter-Society Color Council-National Bureau of Standard").

Tree:

*Vigor.*—Strong; as same as "Okusankichi".

*Predominately spur being.*—Open canopy and light branch density, low pruning requirements.

*Occurence of axillary flower bud.*—Occasional.

*Time of bud break.*—Late.

*Production.*—High productivity.

*Suitable pollinators.*—Cross-compatible with, for example "Kōsui", "Shinsei", and "Niitake".

Branches:

*Thickness.*—Stout. 7.7 mm for current season's growth.

*Length of internode.*—Medium 4.5 cm.

*Lenticel.*—Medium size and density.

*Color.*—ISCC-NBS, grayish yellow brown; 1919.

*Density of pubescence.*—Medium. Mature bark. — Color . . . grayish brown (1617; ISCC-NBS).

Leaves:

*Shape.*—Oval.

*Size.*—Large (14.2 cm×9.9 cm); larger than "Okusankichi".

*Color.*—Dark bluish green (ISCC-NBS, dark olive green; 3708).

*Petiole.*—Medium (3.2 cm).

*Young leaves.*—Reddish brown (ISCC-NBS, deep reddish brown; 0709); and have low pubescence density.

*Fall coloration of leaves.*—Strong reddish yellow (2210; ISCC-NBS).

Flowers:

*The number of flowers in a flower cluster.*—Medium (Flower count of 7).

*Size.*—Large (36.9 mm).

*Color.*—White; white at the pit of a fat bud.

*Color of petals.*—White.

*Shape of petals.*—Round.

*Notch of margin of petals.*—Few.

*Number of petals.*—5.

*Color of anther.*—Strong pink (NSCC-NBS, dark purplish pink; 9511).

*Amount of pollen.*—Medium.

*Flowering time.*—Late in the season; almost the same time as "Okusankichi".

Fruit:

*Size.*—Uniform; about 607 g; slightly smaller than "Okusankichi"; 108 mm diameter; 92 mm height.

*Shape.*—Circular shape with a medium wide middle stalk cavity and a wide medium-deep calyx end, and with good fruit uniformity.

*Color of skin.*—Yellow-reddish-brown (NSCC-NBS, strong orange yellow; 1913).

*Calyx lobes.*—Deciduous.

*Dot size and density.*—Medium for the market class.

*Color of flesh.*—White.

*Flesh.*—Soft, crisp, and juicy. The firmness is about 3.5 Lbs. (according to Magness-Taylor pressure tester index); this is almost the same firmness as "Okusankichi".

*Length of peduncle.*—Long, 3.7 cm.

*Thickness of Peduncle.*—Large. 4.0 mm.

*Shape of core.*—Short, conical.

*Size of core.*—Medium (core/fruit=0.39, at transverse diameter).

*Seed cells.*—5.1 cells per fruit, about 1.29 seeds per cell.

*Shape of seed.*—Oval.

*Taste.*—Moderate sweetness: the sugar content of the fruit juice is about 11.7% (which is slightly higher than "Okusankichi"); a medium acidity that is lower than that of "Okusankicih", the pH of the fruit juice is about 4.32, and there is no astringency, and no aromatic flavor.

*Maturity.*—Ripens late in the season, (about 2 weeks earlier than "Okusankichi", (e.g., from late-October)), in the central Kntō district, Japan.

*Use.*—Suitable for dessert.

*Keeping quality.*—Can be kept for about 20 days (which is shorter than "Okusankichi"), at 25° C.

*Resistance to pests and diseases.*—Has a strong resistance to black spot diesease, (with no occurrence of the disease to date); and is not sensitive to pear necrotic spot.

*Cold resistance.*—Has almost the same cold resistance as that of other Japanese pears.

*Core breakdown.*—Few.

*Water core.*—Low.

*Fruit cracking.*—None.

*Culture.*—The shape and uniformity of the fruit shows a tendency to be varied. However, these problems can be solved by usual fruit thinning methods.

This new variety of Japanese pear tree is cultivated and kept at our farm located at 2-1, Fujimoto, Tsukuba-shi, Ibaraki-ken, Japan.

Since the new variety, "Hougetsu", has a strong resistance to diseases which generally attack pear trees; has high productivity and an excellent dessert quality, and since the harvesting stage of this fruit is late in the season, trees of this variety can be conveniently and easily cultivated in various agricultural districts.

We claim:

1. A new and distinct variety of Japanese pear tree, substantially as illustrated and described herein, characterized over known Japanese pear trees by having high vigor, a well maintained spur, high productivity, strong resistance to black spot disease, no sensitivity to pear necrotic spot disease, dark bluish green leaves and white flowers, a large number of fruit, the fruit having yellow-reddish-brown skin and a circular shape; and a flesh which is white in color, soft, crisp and very juicy, with moderate sweetness, medium acidity, no astringency, and no aromatic flavor; with the harvesting stage of the fruit being late in the season.

* * * * *

Pedigree of the 'Hougetsu' pear.